(12) United States Patent
Huang

(10) Patent No.: US 8,883,505 B2
(45) Date of Patent: *Nov. 11, 2014

(54) GENETIC MATERIAL MANIPULATION TECHNIQUES AND PRODUCTS THEREOF

(71) Applicant: Yao-Xiong Huang, GuangZhou (CN)

(72) Inventor: Yao-Xiong Huang, GuangZhou (CN)

(73) Assignee: Geneforge Limited, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 13/684,490

(22) Filed: Nov. 23, 2012

(65) Prior Publication Data

US 2013/0078723 A1    Mar. 28, 2013

Related U.S. Application Data

(63) Continuation-in-part of application No. 12/622,427, filed on Nov. 19, 2009, now Pat. No. 8,318,494.

(30) Foreign Application Priority Data

Nov. 19, 2008  (CN) .......................... 2008 1 0219234
Nov. 17, 2009  (WO) ................ PCT/CN2009/074998

(51) Int. Cl.
   *C12N 15/87*  (2006.01)
   *B23K 26/32*  (2014.01)
   *B82Y 5/00*  (2011.01)
   *B23K 26/40*  (2014.01)
   *C12N 15/90*  (2006.01)
   *A61K 48/00*  (2006.01)

(52) U.S. Cl.
   CPC ............ *C12N 15/87* (2013.01); *B23K 26/3246* (2013.01); *B82Y 5/00* (2013.01); *B23K 26/4035* (2013.01); *C12N 15/90* (2013.01); *A61K 48/00* (2013.01); *B23K 26/403* (2013.01)
   USPC ......................................................... 435/446

(58) Field of Classification Search
   CPC .......... B82Y 5/00; C12N 15/87; C12N 15/90; B23K 26/404; Y10S 430/146
   See application file for complete search history.

(56) References Cited

U.S. PATENT DOCUMENTS 8,318,494 B2 * 11/2012 Huang .......................... 435/446

OTHER PUBLICATIONS

Vorobjev et al (Biophysical Journal. 1993. 64:533-538).*

* cited by examiner

*Primary Examiner* — Scott Long
(74) *Attorney, Agent, or Firm* — James Christopher Schroeder

(57) ABSTRACT

The presently claimed invention applies to a genetic material processing and manipulation method and related product. The claimed invention relates to a method for changing the inherited characteristics of a cell through micro-beam chromosome modification. In one preferred embodiment, improvements to 'genomic surgery' are applied to modify source cell genetic material (101). Source cell (106) is stabilized through micro-pipette (102) applied negative pressure. Excised genetic material (101) undergoes a pre-cutting manipulation step (205) to enhance subsequent genetic manipulation. In an additional embodiment genetic material manipulation is aided by a spindle cutting step (303). The presently claimed invention provides a high quality alternate approach to directed genetic recombination without requiring the use of restriction enzymes and is used for chromosomal repair, removal of defects and new organism creation.

21 Claims, 2 Drawing Sheets

GENETIC MATERIAL MANIPULATION TECHNIQUES AND PRODUCTS THEREOF

CROSS REFERENCE TO RELATED APPLICATIONS

This application is a continuation-in-part of and claims priority to co-pending U.S. patent application Ser. No. 12/622,427 filed on Nov. 19, 2009 entitled "Genetic material and chromosomal processing and manipulation methods" the disclosure of which is hereby incorporated by reference, which claims priority to China Application Number 200810219234X filed on Nov. 19, 2008 and to PCT application No. PCT/CN2009/074998 filed Nov. 17, 2009.

BACKGROUND OF INVENTION

1. Technical Field

The claimed invention is related to genetic technology, particularly involving the process of genetic material and chromosomal modification and manipulation.

2. Description of Related Art

Known methods exist for DNA manipulation, but the current methods have inherent limitations. Non-specific irradiation techniques such as those disclosed by Vorobjev et al are distinguishable due to lack of precision and high mutagenic effect.

These techniques have a number of challenges including difficulties to control and access target chromosomes, as well as the inability to repair or remove defective chromosomes. As a consequence, alternate approaches to genetic material micromanipulation are desirable.

BRIEF SUMMARY OF THE INVENTION

According to the presently claimed invention, improvements to a novel method of chromosomal manipulation and modification is hereby disclosed. By applying micro-beam techniques, chromosomes are cut and manipulated to a very fine degree of control. Enhanced cell control is improved by securing the source cell with one or more micropipettes exerting negative pressure on the cell. Exogenous DNA manipulation is further refined through the addition of a pre-cutting step to excise desired chromosome regions. In-vivo chromosomal manipulation is also further improved through chromosomal pre-treatment.

Through the use of the presently claimed invention, genetic material is modified so that living cells are modified to alter life activities and functions by control of cellular metabolic processes and alter gene transcription. Moreover, in particular embodiments, desired chromosomes, chromosome fragments, or modified genetic material of exogenous origin are introduced into cells so that new genes are expressed and with cell division the newly introduced traits are passed to progeny cells.

An additional objective of the presently claimed invention is the use of cell spindle cutting to enhance chromosome manipulation.

BRIEF DESCRIPTION OF THE SEVERAL VIEWS OF THE DRAWING

FIG. 1 is the application of the presently claimed invention by microscopic view of the process as applied to target chromosomes of which:

FIG. 1 (a) shows micropipette secured source cell with genetic material released;

FIG. 1 (b) shows target chromosomes;

FIG. 1 (c) shows target chromosome fragment being cut by micro-beam;

FIG. 1 (d) shows the cut chromosome fragment being captured by another micro-beam;

FIG. 1 (e) shows the fragment being transferred by micro-beam to the vicinity of another chromosome;

FIG. 1 (f) shows the fragment being positioned with another chromosome for welding;

FIG. 1 (g) shows the welding of the two fragments by micro-beam.

DETAILED DESCRIPTION OF A PREFERRED EMBODIMENT

Figure 1:
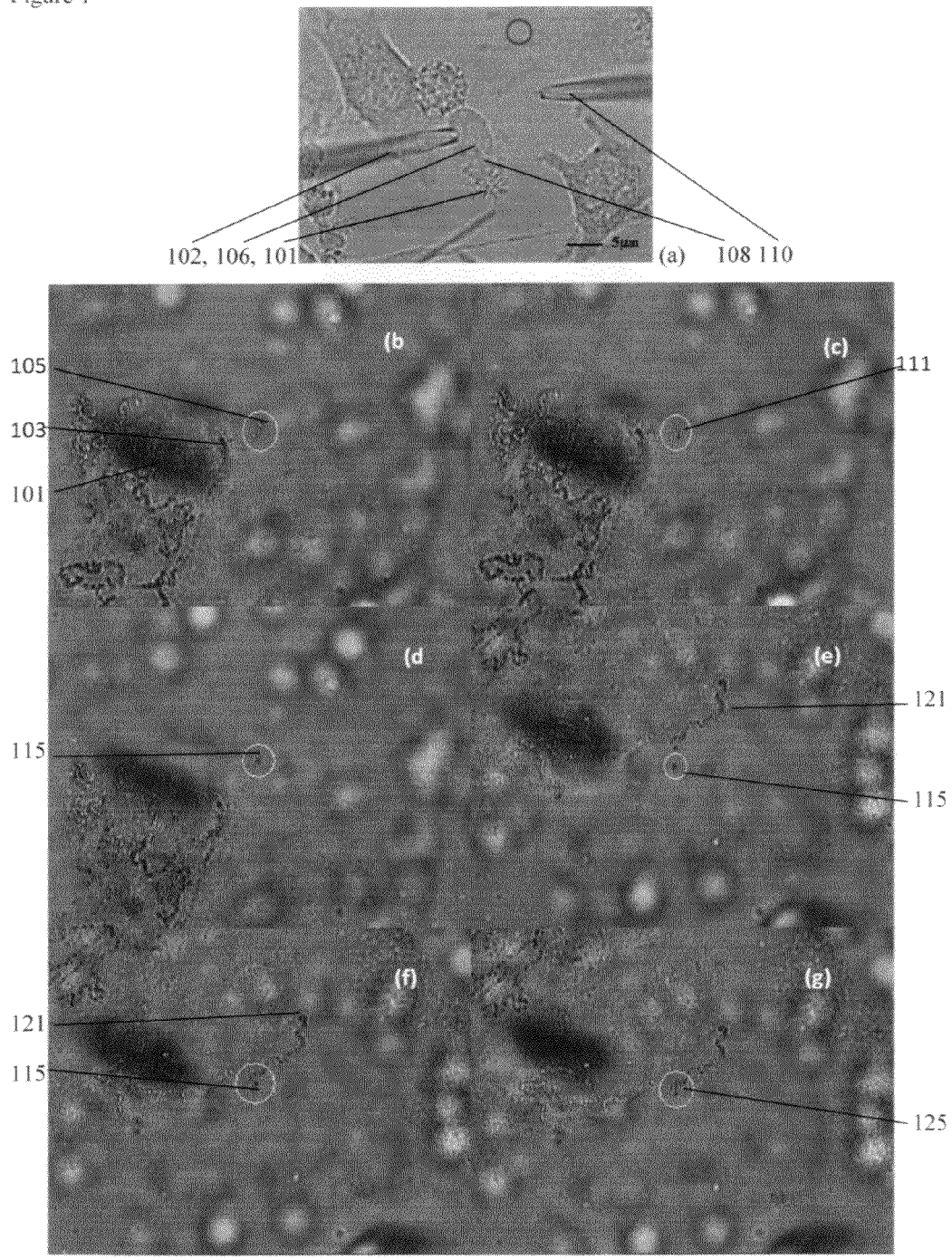

The following examples and drawings depict an implementation of the presently claimed invention in further detail. In a first illustrative example:

Securing step one is illustrated by FIG. 1(a) which shows source cell (106) secured by micropipette (102) to release source genetic material (101). In this illustrative example, source cell (106) is at metaphase in mitosis with chromosomes obviously seen. Micropipette (102) with a diameter about 25%-80% of the diameter of source cell (106) holds source cell (106) with a negative pressure. By using a pulsed nitrogen laser beam with wavelength of 337 nm (not shown), a selected edge of the cell is cut (in an alternative embodiment a hole is drilled) at cutting site (108) in excising step two. While the focus of the beam will vary depending on the physical characteristics and thickness of the cell cut, in a preferred embodiment an energy density of $50 \times 10^6$ $J/m^2 \sim 400 \times 10^6$ $J/m^2$ is desirable. The cutting/drilling process is repeated on a particular target site as needed. The membrane of the target cell is slit, the source genetic material chromosomes (101) are released from cutting site (108) as shown in FIG. 1(a). Using optical tweezers (not shown) with a preferred power density of $10 \times 109$ $W/m^2 \sim 200 \times 109$ $W/m^2$ and one or more micropipette (110) to manipulate source cell genetic material (101) to separate chromosomes (101). Once separated, optical tweezers (not shown) are used to hold source cell genetic material chromosome (101) which is in Brownian motion in solution for cutting or welding. In alternate embodiments optimized for plant cells such as garlic tip root cells, plant source cell (not shown) is selected in mitosis anaphase and with chromosomes obviously seen. In an additional alternate embodiment optimized for yeast cells, a diploid yeast cell or budding yeast cell with chromosomes obviously seen is selected but for yeast cutting site (not shown) the yeast budding site (not shown) is used to excise yeast genetic material (not shown). The cell in FIG. 1(a) is for illustration purposes only as the technique can be performed on any type of cell.

Cutting step three is illustrated by FIG. 1(b) which shows source genetic material (101) containing chromosomes (103, 105) prepared for cutting. Sample (101) is placed in an inverted microscope stage (not shown). Using a wavelength of 337 nm, the pulsed nitrogen laser beam is focused through the microscope objective to a micro-beam with a diameter of 0.6-3 microns in diameter. The energy density of the beam is adjusted to $168 \times 10^6$ $J/m^2$. FIG. 1(c) depicts chromosome alignment and cutting at the site of exposure (111). The chromosome in FIGS. 1(b)-1(g) is for illustration purposes only as the technique can be performed on any type of chromosome.

Positioning step four is illustrated by FIG. 1(d) and FIG. 1(e) where laser irradiation used for cutting is turned off and another laser with wavelength of 1064 nm from a continuous single-mode Nd: YAG laser is introduced into the microscope. The Nd: YAG laser is focused to a micro-beam with a diameter of 0.6-3 microns by the objective of the microscope, so its power density is $63 \times 10^9$ W/m$^2$ when its output power is adjusted to 50 mW and acts as optical tweezers. Through the use of the optical tweezers the cut down chromosome segment (115) is captured, and then moved close to the second chromosome (121). FIG. 1(f) depicts the positioning and alignment of the fragment (115) for contact with the second chromosome (121).

Welding step five is illustrated by FIG. 1(g) where a wavelength of 337 nm pulsed nitrogen laser beam (not shown) is focused through a microscope objective (not shown) into a micro-beam with a diameter of 0.6-3 microns in diameter. In the illustrative example, the beam's energy density is adjusted to $152 \times 10^6$ J/m$^2$. The two chromosomes are radiated with the light beam for 18 seconds, after which the two chromosomes are firmly welded to one (125).

Relocation step six uses a laser beam with a wavelength of 337 nm and an energy density of $210 \times 10^6$ J/m$^2$ to perforate a hole (not shown) on receptor cell (not shown). Micro-tube control technology is then applied to carry the welded chromosome through the micro-pore into the receptor cell then injects the welded chromosome segment by injection.

Figure 2:
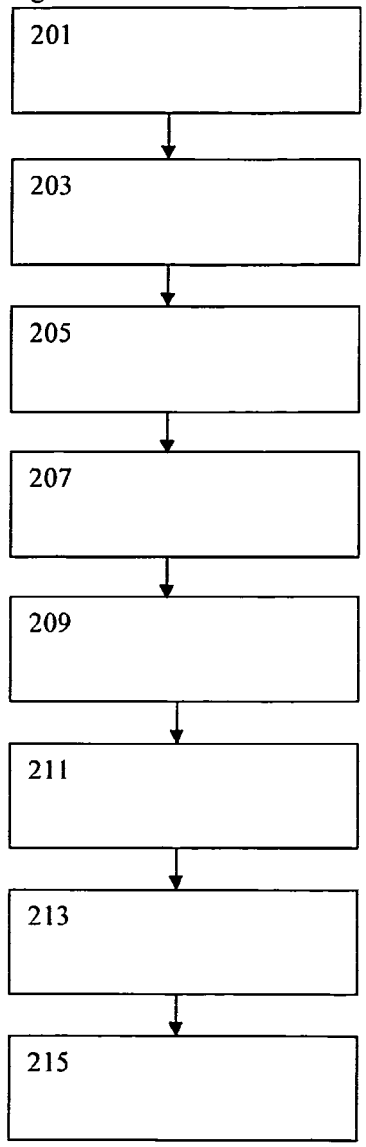
FIG. 2 is a flow diagram according to the claimed invention.

FIG. 2 is a flow diagram according to the claimed invention. Source cell securing step (201) is followed by excising step (203). Genetic material may be separated by an optional genetic material separation step (205). Cutting step (209) cuts source genetic material and may be enhanced by an optional spindle cutting step (207). The cut spindle aids in chromosome separation as well as in subsequent chromosome welding. Positioning step (211) positions the genetic material fragments (not shown) for joining during welding step (213). After welding, the newly joined genetic material composition can optionally be inserted into a target cell (not shown) by repositioning step (215).

Figure 3:
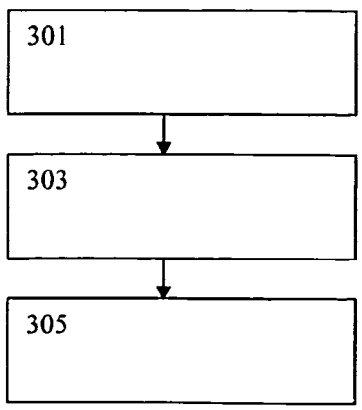
FIG. 3 is a flow diagram according to the claimed invention.

FIG. 3 illustrates another optimization of the claimed technique wherein source genetic material is optimized through spindle cutting and manipulation.

Targeting step (301) locates the desired spindle for cutting.

Spindle cutting step (303) cuts the mitotic spindle to assist in chromosome separation and can be used as an aid in chromosome welding as well. As a direct result of spindle cutting step (303), chromosomes (not shown) are easier to pull apart during manipulation step (305).

Spindle cutting and manipulation may be performed in two ways. When cutting the spindle inside the cell, the source chromosome is then easier to separate and manipulate to another location for genetic welding to another chromosome inside the cell. Prior to genetic welding the target chromosome may require spindle cutting and manipulation as well.

Spindle cutting and manipulation may be performed on chromosomes which have been excised from a source cell. Spindle cutting and manipulation frees the chromosome for moving the source chromosome to another target chromosome for genetic welding. The target chromosome may be of exogenous origin and may require spindle cutting and manipulation as well.

Using a similar technique during chromosome welding the spindle can be used to aid in manipulating the chromosome prior to genetic welding. The later benefit of spindle cutting is the use of the cut spindle in moving the cut chromosome into position for genetic welding.

The illustrated examples depict selected ways to implement the presently claimed invention, but the presently claimed invention may also be applied in a manner not covered by the above-mentioned cases. The examples are provided by way of illustration and not by restriction of the implementation of the claimed invention. Other approaches may also be applied which do not deviate from the essence and spirit of the presently claimed invention. Foreseeable changes, modifications, substitutions, combinations or simplifications can be applied as equivalent methods and are included in the presently claimed invention within the scope of protection.

I claim:

1. A genetic recombination method, comprising the steps of:
   securing source cell with a micropipette exerting negative pressure,
   micro-beam cutting source genetic material
   acquiring source genetic material,
   transporting source genetic material to a target location adjacent to target genetic material, and
   micro-beam welding said source genetic material to said target genetic material to create combined genetic material.

2. The method of claim 1 additionally comprising a micro-beam excising step after securing wherein micro-beam excising said source cell releases source genetic material.

3. The method of claim 2 wherein said source genetic material is exogenous to said target genetic material.

4. The method of claim 3 wherein said micro-beam excising step is made with a laser beam having an energy density of $50 \times 10^6$ J/m$^2$~$400 \times 10^6$ J/m$^2$.

5. The method of claim 1 wherein said securing step is performed with a pipette with an internal diameter about 25%-80% of the diameter of the source cell.

6. The method of claim 1 additionally comprising a genetic material separation step after said micro-beam cutting step wherein source genetic material chromosomes are separated with optical tweezers.

7. The method of claim 2 additionally comprising a genetic material separation step after said micro-beam cutting step wherein source genetic material chromosomes are separated with micromanipulators.

8. The method of claim 6 wherein said genetic material separation step is performed with optical tweezers having a power density of $10 \times 10^9$ W/m$^2$~$200 \times 10^9$ W/m$^2$.

9. The method of claim 1 additionally comprising a spindle cutting and manipulation step prior to micro beam cutting step.

10. The method of claim 9 additionally comprising a spindle and chromosome manipulation step prior to spindle cutting step wherein the chromosome and spindle are manipulated inside the cell with optical tweezers.

11. The method of claim 2 additionally comprising a spindle cutting and manipulation step prior to micro beam cutting step.

12. The method of claim 11 additionally comprising a spindle and chromosome manipulation step prior to spindle cutting step wherein the chromosome and spindle are manipulated outside the cell with optical tweezers and micropipette.

13. The combined genetic material product created by the process of claim 1.

14. The method of claim 1 wherein said source cell is not independently attached to a substrate.

15. The method of claim 2 wherein optical tweezers with a power density of $10\times10^9$ W/m$^2$~$200\times10^9$ W/m$^2$ accompanying with micropipette manipulation is used to separate source genetic material.

16. The method of claim 1 wherein optical tweezers are used to hold target genetic material in Brownian motion in solution.

17. The method of claim 2 wherein optical tweezers are used to hold target genetic material in Brownian motion in solution.

18. The method of claim 1 wherein optical tweezers are used to arouse part of target genetic material without adhering to a substrate.

19. The method of claim 1 wherein optical tweezers are used to hold both source and target genetic material during micro-beam welding.

20. A genetic recombination method, comprising the steps of:
   securing source cell by adhesion,
   micro-beam cutting source genetic material
   acquiring source genetic material,
   transporting source genetic material to a target location adjacent to target genetic material, and
   micro-beam welding said source genetic material to said target genetic material to create combined genetic material.

21. The method of claim 20 additionally comprising a micro-beam excising step after securing wherein micro-beam excising said source cell releases source genetic material.

\* \* \* \* \*